United States Patent
Nankai et al.

[11] Patent Number: 5,266,179
[45] Date of Patent: Nov. 30, 1993

[54] QUANTITATIVE ANALYSIS METHOD AND ITS SYSTEM USING A DISPOSABLE SENSOR

[75] Inventors: Shiro Nankai, Hirakata; Mariko Kawaguri, Moriguchi; Toshihiko Yoshioka, Osaka; Haruhiro Tsutsumi, Ehime; Kyozo Terao, Matsuyama; Naoki Tanimoto, Ehime; Masahiro Yoshioka, Takatsuki; Hiroshi Hyodo, Kusatsu; Takatoshi Uchigaki, Souraku, all of Japan

[73] Assignees: Matsushita Electric Industrial Co., Ltd., Osaka; Kyoto Daiichi Kagaku Co., Ltd., Kyoto, both of Japan

[21] Appl. No.: 733,130

[22] Filed: Jul. 19, 1991

[30] Foreign Application Priority Data

Jul. 20, 1990 [JP] Japan ................................ 2-193449
Jul. 20, 1990 [JP] Japan ................................ 2-193646
Jul. 15, 1991 [JP] Japan ................................ 3-173737

[51] Int. Cl.$^5$ ........................................... G01N 27/26
[52] U.S. Cl. ................................ 204/401; 204/403; 204/416; 204/418; 204/419
[58] Field of Search ............... 204/401, 400, 403, 416, 204/418, 419

[56] References Cited

U.S. PATENT DOCUMENTS

| | | | |
|---|---|---|---|
| 4,622,844 | 11/1986 | Bienkowski | 204/401 |
| 4,713,165 | 7/1987 | Conover et al. | 204/403 |
| 4,868,508 | 9/1989 | Ohishi | 204/401 |

FOREIGN PATENT DOCUMENTS

| | | |
|---|---|---|
| 0230472 | 6/1986 | European Pat. Off. |
| 0220888 | 10/1986 | European Pat. Off. |
| 3822530 | 7/1988 | Fed. Rep. of Germany |
| 61-294351 | 12/1986 | Japan |
| 9000738 | 7/1989 | PCT Int'l Appl. |

*Primary Examiner*—John Niebling
*Assistant Examiner*—Bruce F. Bell

[57] ABSTRACT

A sensor 13 is inserted into a connector 14. A constant voltage required to obtain a response current is applied across the connector 14 by a voltage applying source 15 at timings required. A response current of the sensor 13 inserted into the connector 14 is converted into a voltage by a current-to-voltage converter 16, and the amount thereof is determined by a microcomputer, the analysis results being displayed onto a display unit.

22 Claims, 6 Drawing Sheets

QUANTITATIVE ANALYSIS METHOD AND ITS SYSTEM USING A DISPOSABLE SENSOR

BACKGROUND OF THE INVENTION

1. Field of the Invention

The present invention relates to a quantitative analyzer for measuring such as a glucose level of biological fluid, particularly body fluid.

2. Description of the Prior Art

Various biosensors utilizing a specific catalytic action possessed by enzymes have recently been developed and applied, in particular, in the clinical field. Development of biosensors having an ability of providing rapid and yet precise analytical results have long been desired in view of increasing number of samples and increasing number of items to be tested.

Diabetes mellitus is a disease from which the patient can not completely recover. However, the patient can live a normal life by keeping a concentration of glucose in blood at a normal level. Accordingly, constant retention of the normal glucose level is essential as a treatment of diabetes mellitus. The retention of the normal glucose level may be easily carried out on inpatients under physician's observation.

However, outpatients must conduct self-management in order to keep their blood glucose at a constant normal level. Such self-management includes dietary therapy, ergotherapy, and drug therapy, and the patients usually conduct the self-management on the above-noted two or more items under physician's directions. It is reported that when patients can check by themselves if their blood glucose level analytical results of glucose level in blood is within normal range or not, the self-management can be more effective.

In the treatment of insulin-dependent diabetes mellitus (IDDM), normal blood glucose level is maintained through repeated insulin-injections effected by patients themselves. However, the blood glucose level varies rapidly and considerably depending on caloric intake, dietary time, and injection time, and therefore, it is essential that the patients conduct the measurement of the glucose level by themselves.

Under such circumstances, various portable measurement systems have long been commercially available, which enable diabetes patients to conduct the glucose level measurement by themselves. Blood glucose level is generally determined using such a conventional measurement system in the following manner: whole blood which has been taken from a fingertip or ear lobe using a needle is contacted a test paper containing an enzyme specifically reacting with glucose and a color-producing reagent which develops color based on oxidation-reduction reaction; thereby the reagent and blood glucose react together and produce color, a thickness of which is measured using an exclusive mini-reflectometer analyzer attached to the system; the blood glucose level is determined on the basis of the calibration curve previously prepared and memorized in the analyzer.

However, it has been found that the blood glucose level determined according to the above systems varies greatly depending on patients' manipulation for measurement. Accordingly, Diabetes Associations in many countries have counseled the improvement of the measurement systems. The most important factor causing the above-noted variation of test results is associated with the manipulation needed for removing excessive blood from the test paper after a predetermined time. The removal of excessive blood is usually conducted through wiping with absorbent cotton, removing with a filter paper or rinsing with water, and such procedures bring about test errors in the following manner.

(i) Remaining blood on the test paper due to incomplete removal gives a greater value than the actual value.

(ii) Excessive wiping or rinsing damages the test paper or washes out colored reagent, which gives smaller value than the actual value.

(iii) Inadequate manipulation which brings about shortage of reaction time causes insufficient coloration of the reagent, and mistimed manipulation makes it impossible to completely remove blood because of blood clotting or drying, thereby erroneous test results are obtained.

Moreover, when blood is contacted with the test paper, the command (key input) of the timing for starting the measurement should be effected within an elapse of mistiming from ±2 to 3 seconds. In actual cases (of some patients), however, this mistiming may be 30 seconds to one minute, which can be another factor for the variation of test results, causing less reliability of measured values.

In the last few years there has been commercially available a new measurement system (manufactured by Medisense Inc., commodity name: Exactech) which has solved a main part of the above problems. This system is a pen type system which displays measuring results 30 seconds after its measurement start switch is pressed the moment blood is fed onto its test electrode chip. The system has obviated the need of removing blood and the factors for considerable test errors.

Diabetics, in some cases, have poor blood circulation and are therefore susceptible to infectious disease. This means that a slight wound on their hands or feet may cause suppuration, thus requiring the diabetics to keep themselves clean. Accordingly, equipment and a sensor for collecting blood in the measurement of blood glucose level are preferably provided in disposable form in view of hygienic control rather than used a plurality of times after they are sterilized and stored. This will ensure safety in hygiene and alleviate patients' burden.

As a method that allows a sensor to be disposable, a biosensor has already been proposed which is disclosed in the Japanese Patent Laid Open 61-294351. This biosensor, as shown in FIG. 1, is so constructed that electrode systems 136(136'), 137(137'), and 138(138') made of carbon or the like are formed on an insulating substrate 135 by a method of screen printing or the like, an insulating layer 139 is provided thereon, the electrode systems are covered with a porous body 141 carrying oxidoreductase and electron acceptors, and all these are integrated with a retaining frame 140 and a cover 142. When a sample liquid is dropped onto the porous body, the oxidoreductase and electron acceptors carried by the porous body are dissolved in the sample liquid, causing a reaction to proceed between the enzyme and substrate in the liquid and the electron acceptors to be reduced. After completion of the reaction, the reduced electron acceptors are electrochemically oxidized, and the resulting value of oxidation current is used to determine the concentration of substrate in the sample liquid.

However, in the Exactech, it is necessary to press the measurement start switch, which causes a defect that a considerable extent of mistiming in the measurement cannot be prevented. Moreover, its analyzer, being of pen type, makes its switch formed into one. As a result, since the calibration and adjustment of the analyzer must be carried out using this switch, the key operation involved has been made more complex unexpectedly. Also, since blood is placed onto the test electrode chips tipped by the pen and measurement is conducted without wiping the blood off, the patient is required to keep holding the analyzer during measurement so that the blood will not spill out. The system has therefore been inconvenient to use for the patients.

As described heretofore, since the self-management measurement system of blood glucose level conventionally available requires patients to conduct the command of starting measurement by themselves, it has been accompanied by such a defect that correct test results cannot be obtained depending on patients, manipulation. Moreover, complex key operation has been involved in operation for the calibration and test of the analyzer.

Conventional disposable systems, on the other hand, have been accompanied by such problems that test results may vary or that patients are required to distinguish whether a sensor has already been used or not.

SUMMARY OF THE INVENTION

The present invention has been achieved in view of the foregoing problems, and therefore its essential object is to provide a system and method in which the command of starting measurement can automatically be effected using a sensor having a capillary-shaped portion that obviates the need of removing excessive blood for self-measurement of blood glucose level, and in which calibration and test of the analyzer can be done without key operation.

Another important object of the present invention is to provide such a measurement system further capable of minimizing the variation of test results.

To accomplish these and other objects, the inventors have developed a system and method in which the command of starting measurement can automatically be effected using a sensor having a capillary-shaped portion that obviates the need of removing excessive blood for self-measurement of blood glucose level, the variation of test results can be minimized, and in which calibration and test of the analyzer can be done without key operation.

Now the present invention will be described in detail.

The system of the present invention is used as a set with an exclusive sensor. In one embodiment, the exclusive sensor is a disposable electrode by the amperometric method, while the system is an amperometric analyzer which displays the concentration of glucose calculated using a calibration curve from a measured current value.

In use of the system, with the sensor fitted into a sensor holder of the analyzer, the value of resistance at the electrode is infinity while blood is not supplied. Accordingly, the analyzer distinguishes that the sensor has been fitted into the holder, awaiting blood to be supplied.

When blood is supplied, the resistance value abruptly lowers. The sensor detects this lowering of the resistance value, and distinguishes that blood has been supplied, making the timer of the analyzer start. After a specified time, a constant voltage is applied to the sensor, and the resulting current is measured and converted into a glucose level using a previously set calibration curve, the converted result being displayed as a measured value.

For adjustment of the analyzer, when a resistive chip (adjustment chip) having a sensor-like shape with a constant resistance value is fitted into the holder of the analyzer, it shows the constant resistance value initially. Accordingly, the analyzer distinguishes that it is not the sensor but an adjustment chip, preparing for the adjustment of the analyzer. Adjustment chips include an adjustment mode switching chip, an instrumental error compensating chip, a calibration chip, a test chip, and a unit switching chip.

The instrumental error compensation for the analyzer is carried out in the following manner.

When the adjustment mode switching chip is fitted into the holder of the analyzer, the adjustment mode switching chip shows a constant low resistance value within a range assigned to the adjustment mode switching chip. From this fact, the analyzer distinguishes that it is the instrumental error compensating chip, switching the analyzer to the instrumental error compensation mode.

After adjustment of applied voltage, one of two types of compensating chips having predetermined different resistance values ($R_L$, $R_H$) is fitted into the holder of the analyzer, and the resulting measured value ($R_1$) is stored in the memory. Then, the other compensating chip is fitted into the holder and the resulting measured value ($R_2$) is stored in the memory; thereafter, a subsequent measured value $R_n$ is compensated as a resistance value R according to the following Scheme 1:

$$R = \frac{R_H - R_L}{R_2 - R_1} \cdot R_n + \frac{R_L R_2 - R_H R_1}{R_2 - R_1} \qquad (1)$$

For calibration of the analyzer, when the calibration chip is fitted into the holder of the analyzer, the sensor initially shows a constant resistance value within a range assigned to the calibration chip. From this fact, the analyzer distinguishes that it is the calibration chip, judging the type of calibration curve from the resulting resistance value. Whereas a plurality of types of calibration curves are stored in the analyzer, one type of calibration curve selected thereamong by the calibration chip is set and this is all of the calibration. Since the calibration curve differs depending on the production lot of sensors, sensors are supplied with calibration chips corresponding to each lot.

For testing the analyzer, when a test chip is fitted into the holder of the analyzer, the sensor initially shows a constant resistance value within a range assigned to the test chip. From this fact, the analyzer distinguishes that it is the test chip, displaying the resistance value as converted into the glucose level. The operator then distinguishes whether any abnormality exists in the analyzer according thereto. It may also be arranged that a normal range is previously stored in the analyzer so that existence of any abnormality will be displayed.

For the switching unit in the analyzer, when the unit switching chip is fitted into the holder of the analyzer, the sensor initially shows a constant resistance value within a range assigned to the unit switching chip. From this fact, the analyzer distinguishes that it is the unit switching chip, setting a unit corresponding to the resistance value.

When a used sensor is fitted into the holder of the analyzer, the sensor initially shows a low resistance value because the sensor is made wet by a blood sample, and moreover the value of current flowing through the sensor will vary with the resistance value gradually varying on account of polarization after a voltage is applied. Accordingly, the analyzer distinguishes that it is a used sensor on the basis of the elapsed stability of the current value (resistance value), displaying the fact on its display unit.

Further, the analyzer automatically detects that the sensor has been fitted in position into the reacting state, and interrupts the source of the reaction voltage or the like until the reaction is stabilized. This enables battery consumption to be suppressed.

According to the present invention, since the reaction voltage is applied after the reaction state is stabilized, variation of test results is minimized.

Furthermore, under the condition of high humidity, some sensors (for example, if its porous body 141 (see FIG. 1) is made of any hygroscopic material) are likely made wet due to humidification even though unused. The sensor thus initially shows a low resistance value, which further gradually varies on account of polarization after a voltage is applied. Due to this, the sensor may be incorrectly determined to be a used sensor. To prevent this, the above-noted disposable sensor is further provided with an electrode for detection of liquid junction so that the so-constructed sensor (see FIG. 6) will show a low resistance value when fitted into the sensor holder of the analyzer having such a circuit as shown in FIG. 5, and that it checks whether or not any liquid junction exists at the liquid junction electrode when the resistance value gradually varies, where if any liquid junction exists, it distinguishes that a used sensor has been fitted, while if not, an unused sensor has been fitted, the sensor awaiting blood for measurement to be supplied.

A contact of the analyzer with the electrode for detection of liquid junction may also be used as the above-mentioned adjustment chip and test chip.

DETAILED DESCRIPTION OF THE PREFERRED EMBODIMENTS

A first embodiment of the present invention will be described below with reference to FIGS. 2 to 6.

Figure 1:
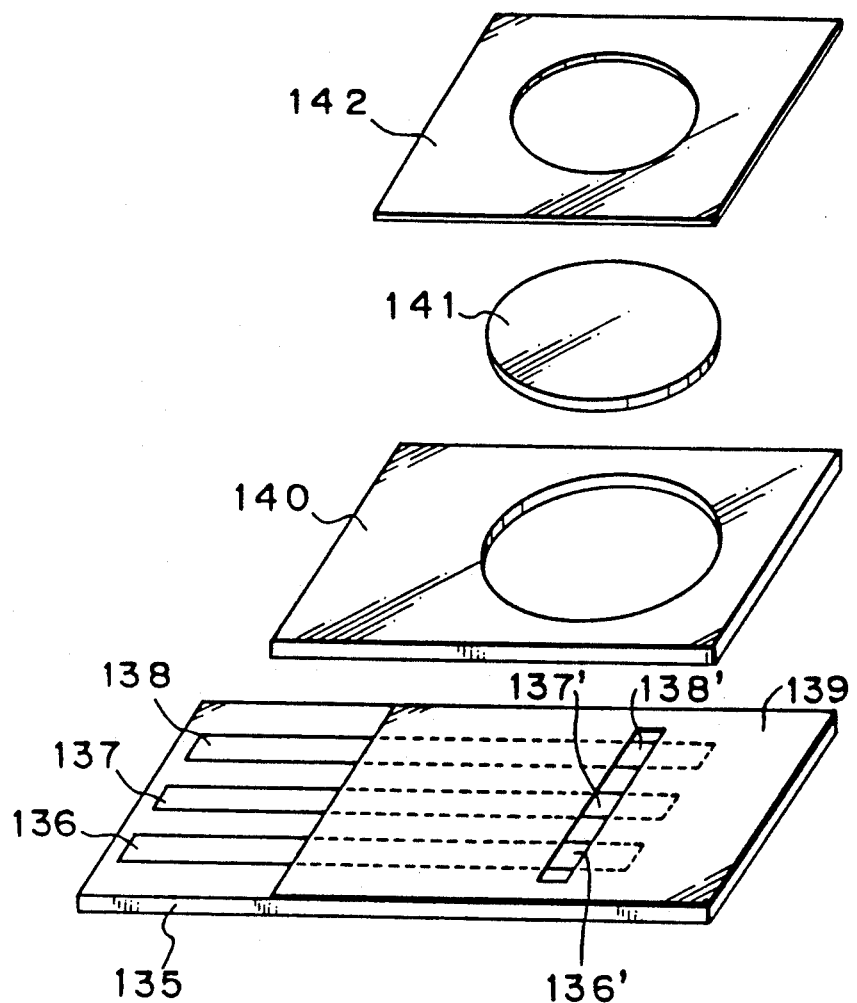
FIG. 1 is an exploded perspective view showing an example of the sensor of a conventional measurement system.
Figure 2:
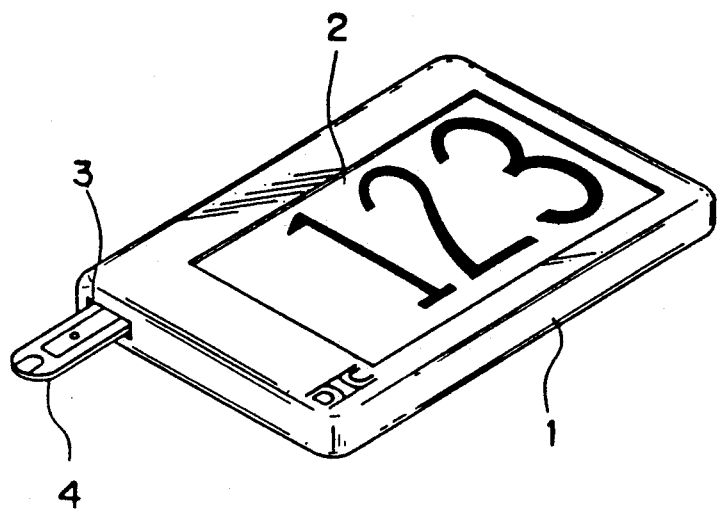
FIG. 2 is a perspective view of an embodiment of a measurement system according to the present invention.
Figure 3:
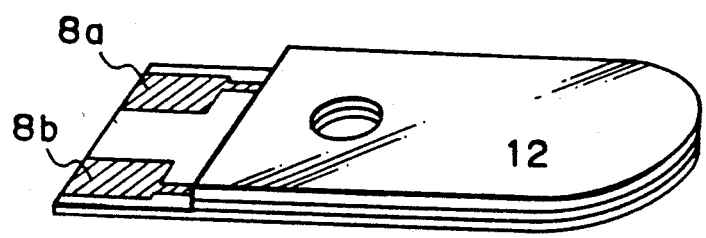
FIG. 3 is a perspective view of a sensor used in the measurement system in FIG. 2.

FIG. 2 shows an example of a system according to the present invention. FIG. 3 shows an example of a sensor to be used in combination with the system of the present invention.

Primary constituents contained in the reagent layer of the sensor are oxidoreductase which is specific for an objective substance in biological body fluid and a redox compound that makes an electron carrier of the enzyme.

As an example, the reaction measurement principle is described below in the case of measuring glucose level.

Glucose oxidase (hereinafter referred to as GOD) is used as an oxidase and potassium ferrocyanide is used as a mediator. When a test sample containing glucose is provided and contacted the sensor, an enzyme reaction occurs between the mediator and the glucose in the presence of GOD as shown in Scheme 2, whereby potassium ferrocyanide is produced in an amount corresponding to the glucose level. Then after an elapse of a specified time, a constant voltage is applied across a lead 8 of the sensor through the circuit used in the present invention. Since the oxidation current obtained therefrom is proportional to the concentration of potassium ferrocyanide produced by the enzyme reaction, i.e. glucose level, the glucose level in the subject body can be determined by measuring the response current.

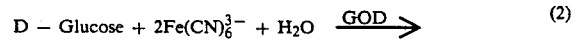

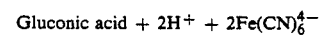

Figure 4:
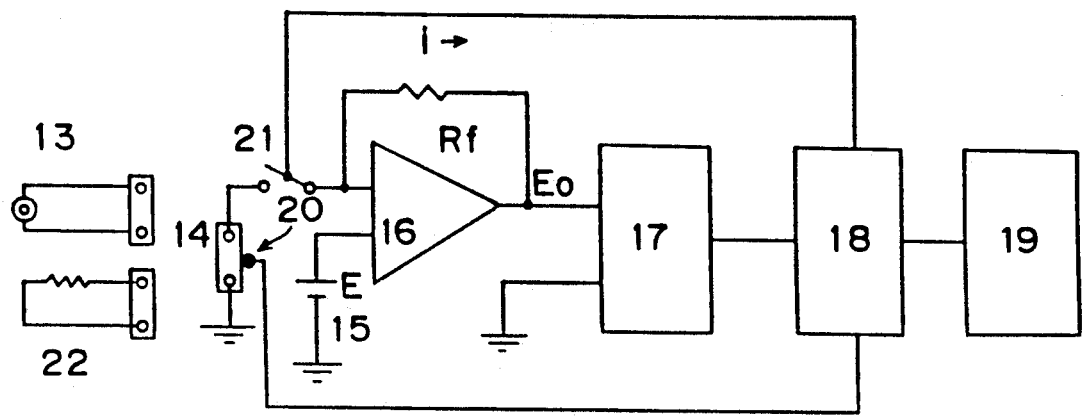
FIG. 4 is a block diagram showing an embodiment of a control unit used in the measurement system in FIG. 2.

FIG. 4 shows a preferred embodiment of the present invention.

Referring to FIG. 4, the operation of the invention is now explained. First, a sensor 13 is inserted into a connector 14. When the insertion of the sensor 13 is detected by an electrode insertion detector switch 20, a switch 21 is closed so that a constant voltage required to obtain a response current is applied across the terminals of the connector 14 by a battery 15 serving as an applied voltage source. The response current of the sensor 13 inserted into the connector 14 is converted into a voltage by a current-to-voltage converter 16, and further inputted into an A/D converter 17.

A microcomputer 18 receives and reads an output signal from the A/D converter 17 and calculates glucose concentration. The sensor 13, enzyme electrode as it is, can be considered to be a type of resistor. For example, if the resistance value of the sensor 13 is Rs, the amplification resistance of the current-to-voltage converter 16 is Rf, and the applied voltage is E, then the output voltage $E_0$ of the current-to-voltage converter 16 can be determined by the following calculation:

$$E_0 = E + i \times Rf = E + (E/Rs) \times Rf$$

Without any sample supplied, since the resistance value Rs of the sensor 13 is extremely high and nearly infinity, the resulting current value i is accordingly extremely low, leading to that the output voltage $E_0$ of the current-to-voltage converter 16 becomes nearly equal to E ($E_0 \approx E$).

On the other hand, with a sample supplied to the sensor 13, since the resistance value Rs of the sensor 13 abruptly lowers with the value of $E_0$ abruptly increasing conversely, the subject body can be sucked and detected by continuously monitoring the output voltage $E_0$ of the current-to-voltage converter 16.

As a result, the measuring timer is automatically started by distinguishing the variation of the output voltage $E_0$ of the current-to-voltage converter 16 with the aid of the A/D converter 17 using the microcomputer 18. With this operation, the switch 21 is simultaneously opened and, after an elapse of a specified time, closed, thereby allowing a measuring result to be obtained.

In order to adjust the analyzer, there is used an adjustment chip 22 having a shape similar to that of the sensor 13 and having a very small constant resistance value which is not to be compared with that of a new sensor (equal to infinity). Since the adjustment chip 22 initially shows a stable, constant voltage when measured, the microcomputer 18 can identify the adjustment chip 22, which is of various types, from the amount of the voltage.

Adjustment chips 22 include ones for uses of adjustment mode switching, instrumental error compensating, calibration, test, unit switching, and the like. When the chip is distinguished to be an adjustment mode switching chip, the analyzer is switched into the adjustment mode, the resistance value of the instrumental error compensating chip is stored, and measured values obtained thereafter are compensated. Normally, the adjustment mode switching chip is used when the analyzer is manufactured or repaired. For example, when the chip is distinguished to be a calibration chip, the microcomputer 18 automatically identifies and selects a calibration curve depending on the resistance value (voltage value) out of a plurality of calibration curves previously stored in the analyzer.

When the chip is distinguished to be a test chip, the microcomputer 18 converts the voltage value into a concentration and displays the result onto a display 2, allowing it to be judged from the amount of the concentration value whether any abnormality in the equipment exists or not.

When the chip is distinguished to be a unit switching chip, the microcomputer 18 changes and converts the concentration value into each concentration unit (for instance, mg/dl or mmol/L), then displaying it.

Table 1 shows a case of distinguishing calibration chips.

| No. of calibration chip | Resistance value (K$\Omega$) | No. of calibration curve |
|---|---|---|
| 0 | 27 | F - 0 |
| 1 | 30 | F - 1 |
| 2 | 33 | F - 2 |
| 3 | 36 | F - 3 |
| 4 | 39 | F - 4 |
| 5 | 43 | F - 5 |
| 6 | 47 | F - 6 |
| 7 | 51 | F - 7 |
| 8 | 56 | F - 8 |
| 9 | 62 | F - 9 |

Figure 5:
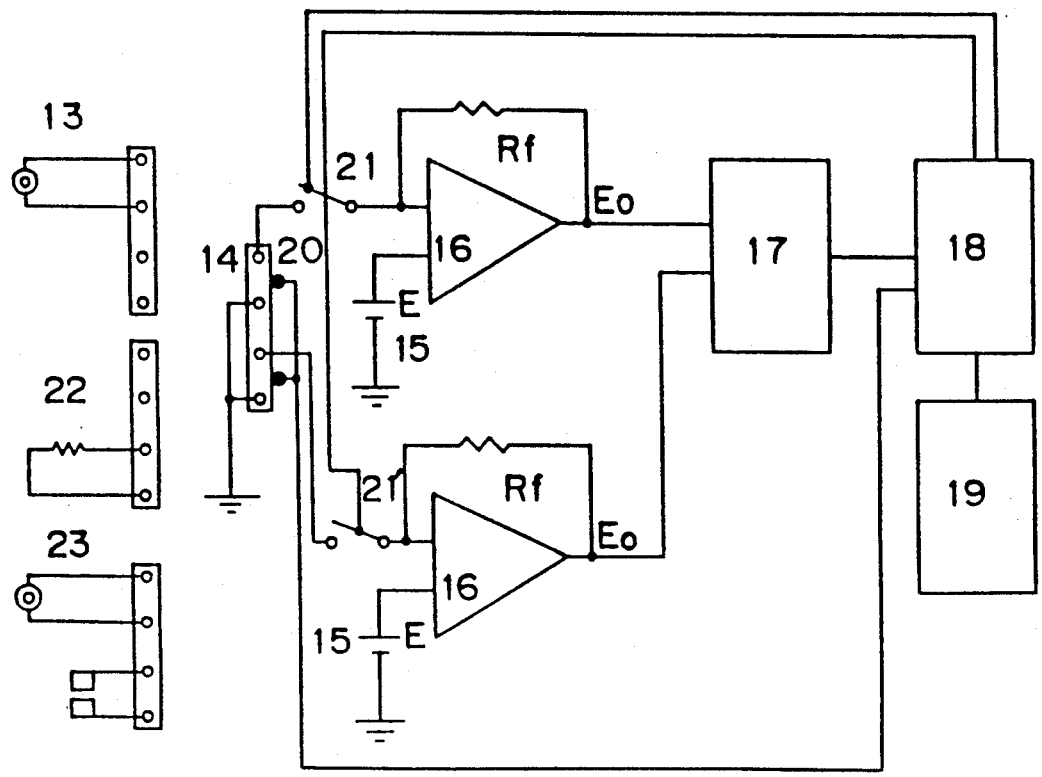
FIG. 5 is a block diagram showing another embodiment of the control unit used in the measurement system in FIG. 2.

Also, the number of terminals of the connector can be increased in such an arrangement as shown in FIG. 5, so that a calibration chip or test chip can be inserted into a terminal other than that into which the sensor 13 is inserted.

However, it is possible that if the identification of calibration chips and test chips is done merely depending on the amount of the resistance value, the chip may be misdistinguished to be a calibration chip or test chip even when a used sensor ss mis-inserted. This is caused by the fact that the resistance value of a used sensor is so low that it may be of the same level as those of the calibration and test chips.

To prevent this misidentification, the following method is adopted: Voltage value $E_{01}$ is measured at the time point when power supply is turned ON with any electrode inserted into a connector of the system, and the voltage value $E_{02}$ is measured once more after the succeeding several seconds. The resulting rate of voltage change $\Delta E$ is calculated and if it shows a change in voltage above a specified level, the chip is distinguished to be a used sensor, which is displayed on the display unit. Otherwise, the chip is distinguished to be a calibration chip or a test chip.

$$\Delta E = \left| \frac{E_{01} - E_{02}}{E_{01}} \right| \tag{3}$$

Figure 6:
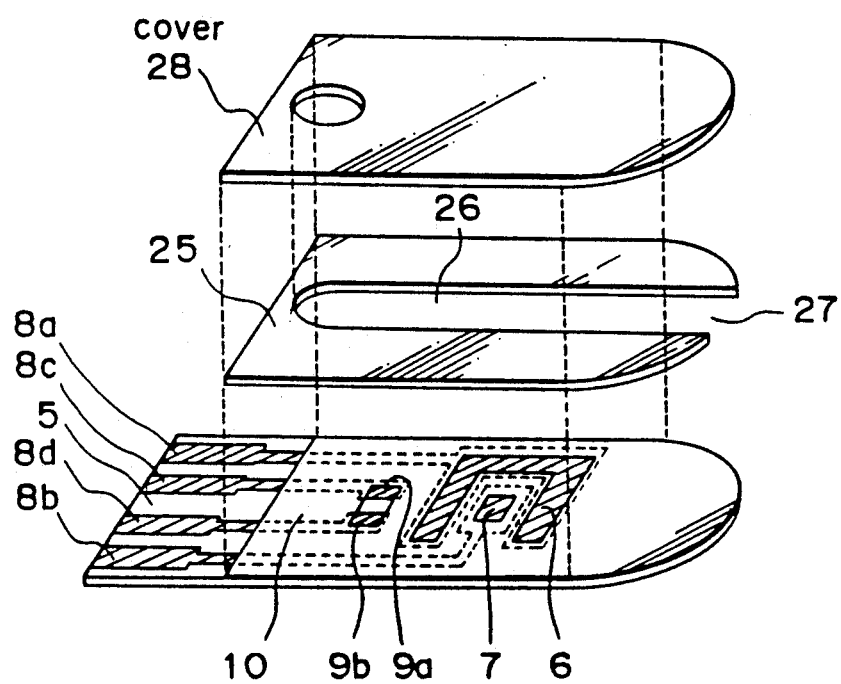
FIG. 6 is an exploded perspective view showing another example of the sensor used in the measurement system in FIG. 2.

If the sensor, even though unused, has a property showing behavior similar to that of a used sensor due to humidification under high humidity condition, electrodes 9a, 9b for detection of liquid junction are provided in combination with the sensor, as shown in FIG. 6. When the above-noted used sensor is subjected to discrimination using both this sensor provided with electrodes for detection of liquid junction and the circuit shown in FIG. 5, it is distinguished that if the resistance value between the electrodes for detection of liquid junction 9a and 9b is infinity, there is no liquid junction, with such a decision made by the electrodes inserted into the connector that the sensor is an unused one, while if the resistance value between the electrodes for detection of liquid junction is low, the sensor is a used one. Meanwhile, the A/D converter 17 is used in combination by turning ON and OFF the switches 21, 21' through the microcomputer 18.

Figure 7:
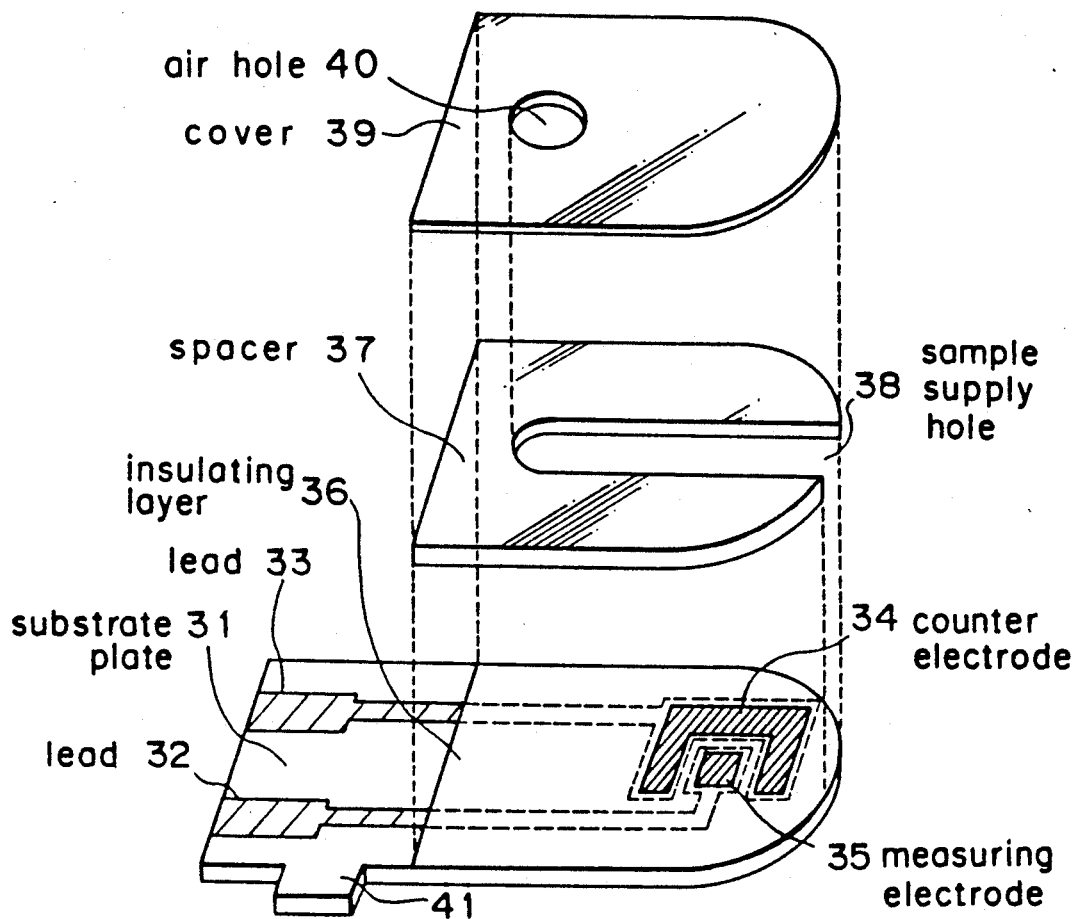
FIG. 7 is an exploded perspective view showing a further example of the sensor used in the measurement system of the present invention.
Figure 8:
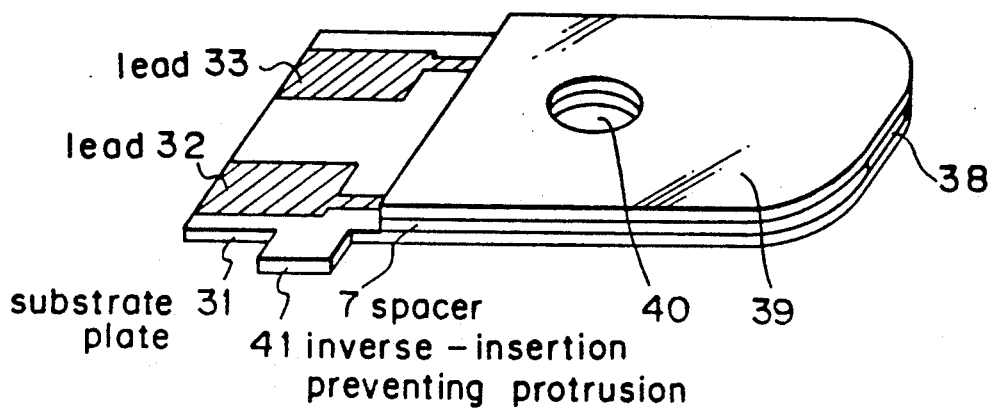
FIG. 8 is a perspective view in which the sensor in FIG. 7 is assembled.

FIG. 7 is a detailed exploded perspective view of the sensor of the measurement system, which is a second embodiment of the present invention, and FIG. 8 is an outline perspective view of the same.

On a substrate plate 31 there is provided counter electrode 34 and a measuring electrode 35, leads 33, 32 connected thereto, and an insulating layer 36. Also, although not shown, there is formed a reaction layer containing an enzyme and a mediator so as to cover the counter electrode and measuring electrode. On the substrate plate 31 there is fixed a cover 39 with a spacer 37 interposed therebetween. Numeral 38 denotes a sample supply hole, through which a sample liquid, i.e. a sample is introduced onto the counter electrode 34 and measuring electrode 35 by capillarity phenomenon. Reference numeral 40 denotes an air hole. In order not to mistake the front and back of the sensor, there is provided an inverse-insertion preventing protrusion 41 so as to protrude from one side end of the sensor, whereby the sensor correctly directed up and down will properly be set with the inverse-insertion preventing protrusion passing through a counter gap of a connector 51, while the sensor, inversely set, will not be inserted into the connector 51 with an obstacle of the inverse-insertion preventing protrusion 41.

Figure 9:
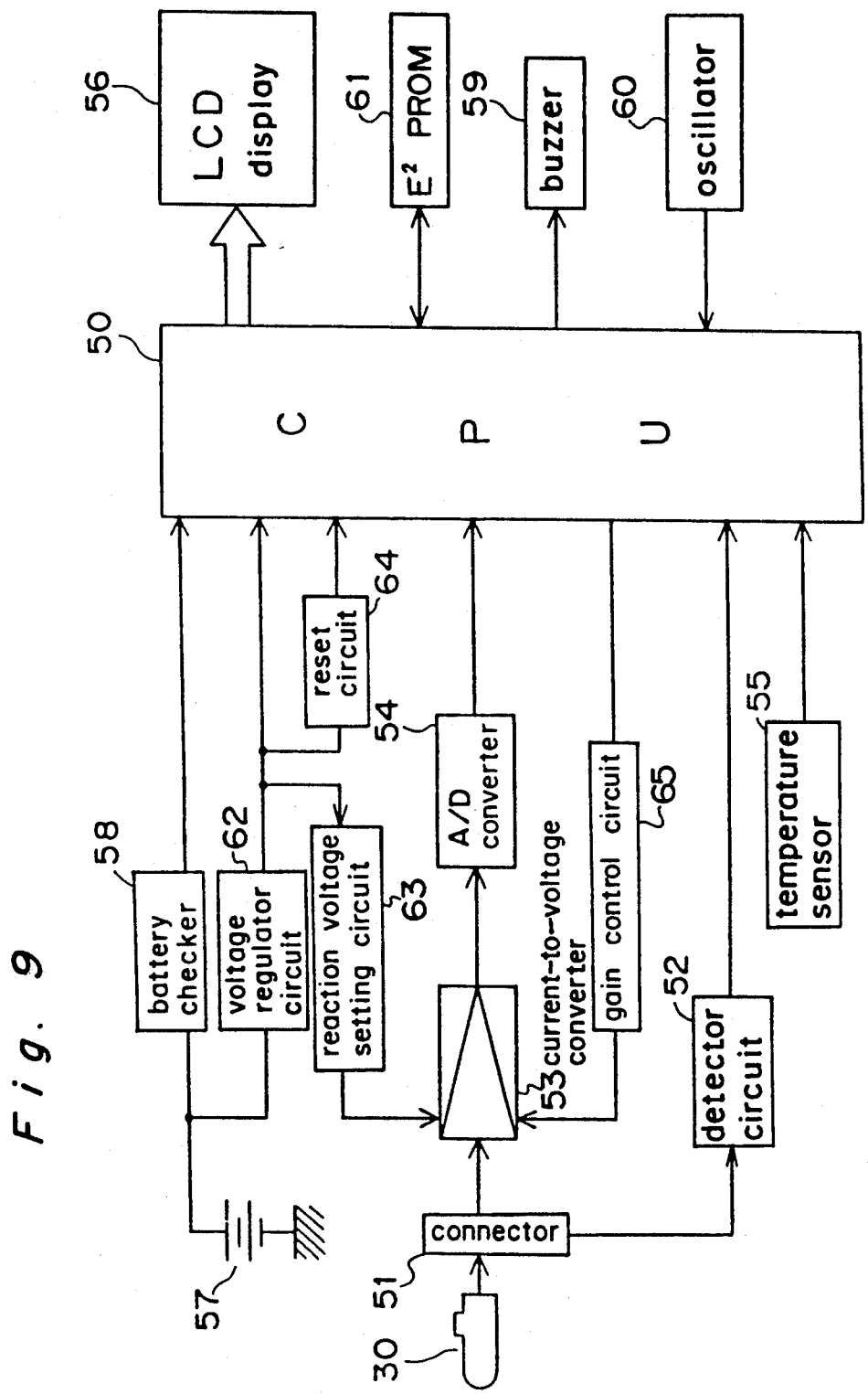
FIG. 9 is a block diagram of a control unit used in combination with the sensor in FIG. 7.

FIG. 9 is a block diagram of the control unit of a measurement system embodying the present invention.

First of all the whole system is activated into the standby state, by initializing CPU 50.

When the sensor 30 is inserted into the connector 51 of the main unit of the system, a detector circuit 52 detects the insertion of the sensor, turning on a current-to-voltage converter 53, an A/D converter 54, a temperature sensor 55, and other components through the CPU 50.

Next, when a sample liquid is supplied to the sensor so as to short-circuit the measuring electrode 35 and the counter electrode 34 with each other, the resistance value will vary to a great extent. The variation is distinguished by the CPU 50 through the A/D converter 54, turning off the current-to-voltage converter 53 with the result that no reaction voltage is supplied. Then, the reaction between the enzyme and sample liquid is allowed to proceed for approximately 55 seconds. During this period, the countdown state is displayed on an LCD display 56. Thereafter, a reaction voltage is applied for approximately 5 seconds, and the current is measured. This measured value is also displayed on the LCD display 56.

The voltage of a battery 57 is checked by the CPU 50 through a battery checker 58 for each one sequence of measurement, so that the voltage, if lower than a specified level, will be displayed onto the LCD display 56. A buzzer indicated by numeral 59 notifies that the sensor 30 has been inserted. An oscillator 60 generates pulses for clocking the operation of the system.

A memory 61 for storing compensation values for each system serves to compensate the variation among systems. Reference numeral 62 denotes a voltage regulator circuit. A circuit 63 serves to set a reaction voltage to be applied to the sensor. A circuit 64 serves to reset the CPU when, for example, measurement is stopped on its way or a battery is changed. A circuit 65 is a gain control circuit.

Although in the above-described embodiments the measurement system is normally in the standby state so that the actions such as applying a reaction voltage are not started until the sensor is inserted into the system main unit, thereby minimizing the number of parts of the system, the present invention is not limited to such an arrangement and allows another such that a standby switch is provided separately.

As described heretofore, according to the present invention, the introduction of samples can automatically be detected and, further, stable measurement with less variation of its results can be realized.

What is claimed is:

1. A quantitative analysis system for measuring a specific component in biological body fluid by an amperometric method, comprising:
    a disposable sensor mounting portion, including a disposable sensor for receiving a sample of the biological body fluid for analysis; and
    means for automatically determining whether a chip mounted on said disposable sensor mounting portion is a sensor for measuring the sample, or an adjustment chip, depending on a measured current value flowing through said system when said chip is mounted on said disposable sensor mounting portion.

2. A quantitative analysis system for measuring a specific component in biological body fluid by an amperometric method, comprising:
    a disposable sensor for receiving a sample of the biological body fluid for analysis; and
    means for automatically distinguishing whether the disposable sensor is used depending on a stability of a measured current value of said disposable sensor.

3. The quantitative analysis system of claim 2, wherein said disposable sensor including an electrode for detecting a liquid junction.

4. A quantitative analysis system comprising:
    means for applying a reaction voltage to a sensor;
    means for detecting that a sample liquid is supplied to said sensor;
    means for interrupting the reaction voltage based on said detection;
    means for reapplying said reaction voltage to said sensor after a specified time period;
    means for detecting a reaction state of said sensor due to reapplication of said reaction voltage; and
    means for displaying the reaction state.

5. The quantitative analysis system of claim 4, said system further comprising means for detecting that said sensor has been mounted on the system, wherein said reaction voltage application means is initiated by said detection.

6. The quantitative analysis system of claim 4 or 5, wherein said reaction voltage application means includes a current-to-voltage converter, for generating a voltage depending on a current generated in said sensor as a result of the application voltage and said reaction state detection means includes a CPU and detects said reaction state based on an output of said current-to-voltage converter and converts said reaction state to a digital value.

7. A quantitative analysis system comprising:
    disposable sensor means, including a capillary shaped portion and an enzyme portion, for receiving a sample liquid for analysis;
    control means, including a connector for said disposable sensor means, for allowing enzymes in said enzyme portion and the sample liquid to react in an absence of a reaction voltage, for automatically applying the reaction voltage to the reaction after a specified time period, and for measuring an oxidation current indicative of a concentration of a constituent part of the sample liquid; and
    calibrating and testing means for calibrating and testing said system without key operation.

8. The quantitative analysis system of claim 7, wherein said system is portable.

9. The quantitative analysis system of claim 7, said calibrating and testing means including,
    means for automatically distinguishing whether said disposable sensor means has been placed in said connector with the sample liquid or without the sample liquid and for distinguishing whether an adjustment chip has been placed in said connector, depending on the measured current.

10. The quantitative analysis system of claim 9, wherein the adjustment chip is an adjustment mode switching chip, an instrumental error compensating chip, a calibration chip, a test chip, or a unit switching chip.

11. The quantitative analysis system of claim 10, wherein when the adjustment chip is the adjustment mode switching chip, which has a constant low resistance with a range assigned to the adjustment mode switching chip in order to adjust the reaction voltage.

12. The quantitative analysis system of claim 11, wherein two instrumental error compensating chips are sequentially inserted in said connector after the adjustment mode switching chip in order to compensate a resistance of said system.

13. The quantitative analysis system of claim 9, wherein the adjustment chip is the calibration chip and said system generates a constant resistance with a range assigned to the calibration chip in order to select an appropriate calibration curve.

14. The quantitative analysis system of claim 9, wherein the adjustment chip is the test chip and said system generates a constant resistance with a range assigned to the test chip in order to identify and abnormalities in said system.

15. The quantitative analysis system of claim 9, wherein the adjustment chip is the unit switching chip and said system generates a constant resistance with a range assigned to the unit switching chip in order to set a unit corresponding to the measured current.

16. The quantitative analysis system of claim 7, said disposable sensing means including a liquid junction detection electrode, said control means monitoring said liquid detection electrode in order to determine whether a liquid junction exists.

17. The quantitative analysis system of claim 10, said disposable sensing means including a mediator, and said mediator contacts blood glucose in the presence of glucose oxidase to produce potassium ferrocyanide, and after the predetermined time, the reaction voltage is applied to said disposable sensing means to produce the oxidation current which is proportional to the potassium ferrocyanide level and representative of the blood glucose level.

18. The quantitative analysis system of claim 10, wherein said enzyme portion acts as a resistor, said control means including, means for determining whether said disposable sensing means or said adjustment chip has been inserted in said connector, voltage means for applying the reaction voltage across said connector, and correcting means for converting the oxidation current into a voltage, said voltage represented by:

$$Eo = E + i * Rf = E + (E/Rs) * Rf$$

where:
Eo = said voltage,
E = the reaction voltage,
Rf = an amplification resistance of said converting means, and
Rs = a resistance value of said enzyme portion.

19. The quantitative analysis system of claim 18, said calibrating and testing means including means for automatically determining the type of adjustment chip according to said voltage.

20. The quantitative analysis system of claim 10, said control means including a second connector for receiving the adjustment chip.

21. The quantitative analysis system of claim 7, said disposable sensing means including, a substrate, including a counter electrode, a measuring electrode, and at least one lead, a insulating layer, a reaction layer, including an enzyme and a mediator which cover said counter electrode and said measuring electrode, a spacer, with longitudinal groove, a cover, with an air hole through which the sample liquid is placed on the reaction layer, and an inverse-inserting preventing protrusion for ensuring said disposable sensing means is correctly oriented in said connector.

22. The quantitative analysis system of claim 7, wherein said control means includes a standby switch for initiating the specified time period.

* * * * *